United States Patent [19]
Roberts

[11] Patent Number: 5,717,993
[45] Date of Patent: Feb. 17, 1998

[54] POST-SURGERY LIP AND CHIN PROTECTOR

[76] Inventor: Bennie Rena Roberts, 3341 Barnsley Loop, Madisonville, Ky. 42431

[21] Appl. No.: 778,263

[22] Filed: Jan. 2, 1997

[51] Int. Cl.⁶ .................... A42B 1/00; A41D 13/00
[52] U.S. Cl. ........................................ 2/9; 128/857
[58] Field of Search ..................... 2/174, 9, 424, 2/425, 206; 128/857, 859, 861; 602/74, 17

[56] References Cited

U.S. PATENT DOCUMENTS

| | | | |
|---|---|---|---|
| 1,297,842 | 3/1919 | Harllee | 128/857 |
| 1,480,780 | 2/1924 | Pauley. | |
| 1,492,387 | 4/1924 | Pool | 128/857 |
| 1,627,618 | 5/1927 | Paul. | |
| 1,678,649 | 7/1928 | Renault | 2/174 |
| 1,715,740 | 6/1929 | Cervelli. | |
| 1,758,286 | 5/1930 | Larson. | |
| 1,810,486 | 6/1931 | Lancaster. | |
| 1,819,076 | 8/1931 | Davies. | |
| 1,820,602 | 8/1931 | Dick. | |
| 2,023,900 | 12/1935 | Rally | 2/174 |
| 2,355,283 | 8/1944 | Diss | 2/174 |
| 2,358,484 | 9/1944 | Torjussen et al. | 2/174 |
| 2,434,078 | 1/1948 | Malerman | 2/174 |
| 2,573,537 | 10/1951 | Bouffard | 2/174 |
| 2,589,504 | 3/1952 | Miller | 128/857 |
| 2,881,442 | 4/1959 | Sowle | 2/9 |
| 2,973,762 | 3/1961 | Koenig | 128/399 |
| 3,126,550 | 3/1964 | Price | 2/174 |
| 3,196,458 | 7/1965 | Keith | 2/9 |
| 3,203,417 | 8/1965 | Helmer | 128/857 |
| 3,527,461 | 9/1970 | Prater | 273/1 |
| 3,815,610 | 6/1974 | Winther | 128/380 |
| 4,040,127 | 8/1977 | Slovitt et al. | 2/174 |
| 4,527,565 | 7/1985 | Ellis | 128/402 |
| 4,559,047 | 12/1985 | Kapralis et al. | 604/291 |
| 5,570,705 | 11/1996 | Burke | 128/857 |

FOREIGN PATENT DOCUMENTS

| | | | |
|---|---|---|---|
| 128068 | 6/1948 | Australia | 128/857 |
| 593217 | 2/1934 | Germany | 128/857 |

*Primary Examiner*—Amy B. Vanatta
*Attorney, Agent, or Firm*—Waddey & Patterson; Laura K. Thomas

[57] ABSTRACT

A post-surgery lip and chin protector is described. The protector includes a barrier section having a sufficient area to cover the lips and chin of the patient. A hole is formed in the barrier section in a position so that the hole will be adjacent to the patient's mouth when the patient wears the protector. A flexible area is formed in the barrier section adjacent to the patient's lips to enable the patient to open and close his mouth while wearing the protector. Finally, the protector includes flanges that project into the patient's mouth and beneath the patient's chin to secure the protector in its desired position. Additionally, the protector can further include a strap that fits around the patient's head when the protector is worn.

12 Claims, 2 Drawing Sheets

POST-SURGERY LIP AND CHIN PROTECTOR

BACKGROUND OF THE INVENTION

The present invention relates generally to a protector for a person's lip and chin; and more particularly to a lip and chin protector for use after a surgical procedure on the person's lip and/or chin.

It will be appreciated by those skilled in the art that there are a variety of surgical procedures wherein the lip and chin of the patient are surgically repaired. Such procedures include cleft palate procedures and cosmetic surgery.

During the recuperation process, it is difficult to adequately protect the area that was subjected to the surgery when the recuperating patient is eating or drinking. It is also difficult to protect the area of the surgery and yet enable the user to speak to other parties.

There have been several attempts to provide articles that protect the lips and chin of a person. One such attempt was disclosed in U.S. Pat. No. 4,404,127, issued to Slovitt et al. on Aug. 9, 1977. This patent describes a device to cover the lips of a user to protect the user's lips from exposure to prolonged sun and wind. However, this article does not offer adequate chin protection and is difficult to adequately secure in the desired position.

Another such attempt was described in U.S. Pat. No. 2,589,504, issued to Miller on Jun. 24, 1950. This patent describes a protector for the lips and teeth with particular application in football. Thus, this article does not allow the wearer to eat or drink when wearing the protector.

What is needed, then, is a post-surgery lip and chin protector that allows movement of the patient's mouth so that the recuperating patient can eat, drink or talk while wearing the protector. Such a protector is presently lacking in the prior art.

SUMMARY OF THE INVENTION

Accordingly, a post-surgery lip and chin protector is described herein. The post-surgery lip and chin protector of this invention comprises a barrier section having sufficient area to cover the lips and chin of the user; an opening formed in the barrier section, the opening located so as to be adjacent to the mouth of the user when the protector is donned by the user; a flexible area adjacent to the lips of the user; and means for securing the protector to the lips and chin of the user.

The means for securing the barrier section to the lips and chin of the user can comprise a flange extending rearward from the barrier section so that the flange can fit around at least one of the user's lips. An additional flange can extend rearward from the barrier section, said flange adapted to fit behind the other of the user's lips. A strap can also be mounted to the barrier section, said strap adapted to fit around the user's head. Additionally, the means for securing the barrier section to the lips and the chin of the user can further comprise a flange extending rearward from the barrier section near the bottom of the barrier section, said flange fitting beneath the user's chin.

It is an object of the invention to provide a post-surgery lip and chin protector.

It is yet a further object of this invention to provide a post-surgery lip and chin protector that protects the lip and chin areas that were the subject of surgery while the recuperating patient is eating or drinking.

It is yet a farther object of this invention to provide a post-surgery lip and chin protector that prevents food and drink from entering the healing area where the surgery was performed.

It is still a further object of this invention to provide a post-surgery lip and chin protector that includes a flexible area adjacent to the patient's mouth to allow movement of the patient's mouth.

It is still a further object of this invention to provide a post-surgery lip and chin protector that includes extensions that fit into the patient's mouth or beneath the patient's chin to secure the protector to the patient.

Other objects and advantages will be apparent from the foregoing description.

DESCRIPTION OF THE PREFERRED EMBODIMENT

Figure 1:
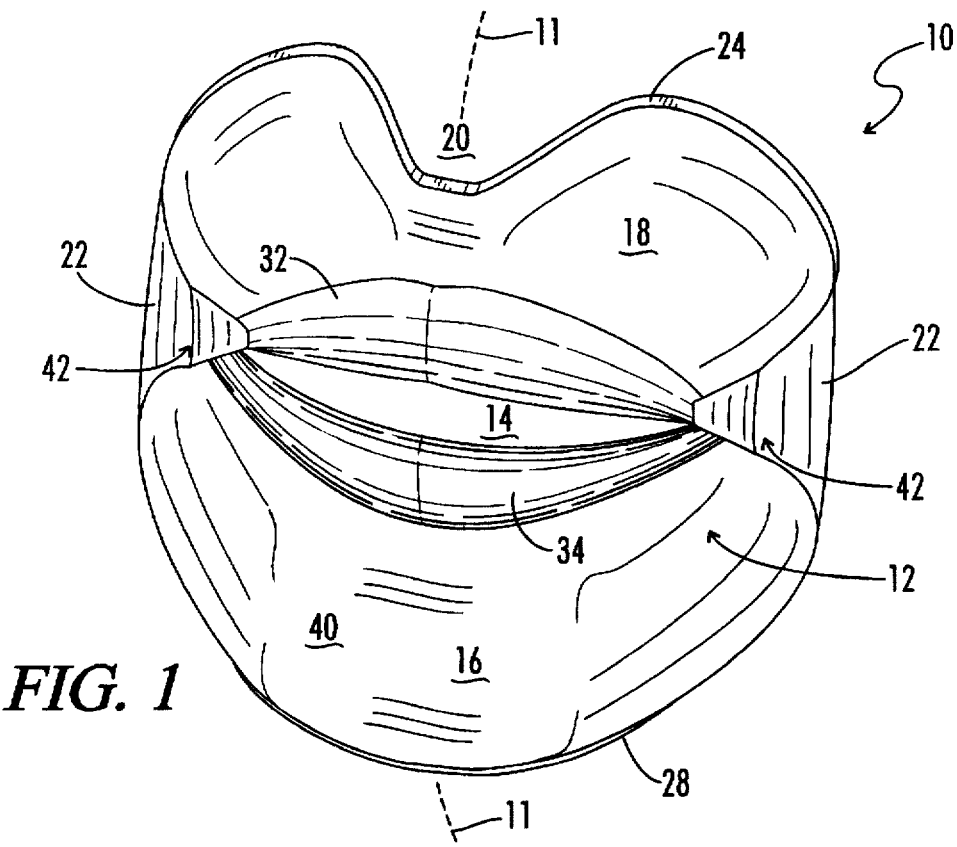
FIG. 1 is a perspective view of the lip and chin protector of the present invention.

Referring now to the drawings, wherein like reference numerals refer to like parts throughout, the post-surgery lip and chin protector of this invention is referred to generally at 10. Protector 10 comprises barrier section 12, flexible areas 22, and opening 14.

Figure 2:
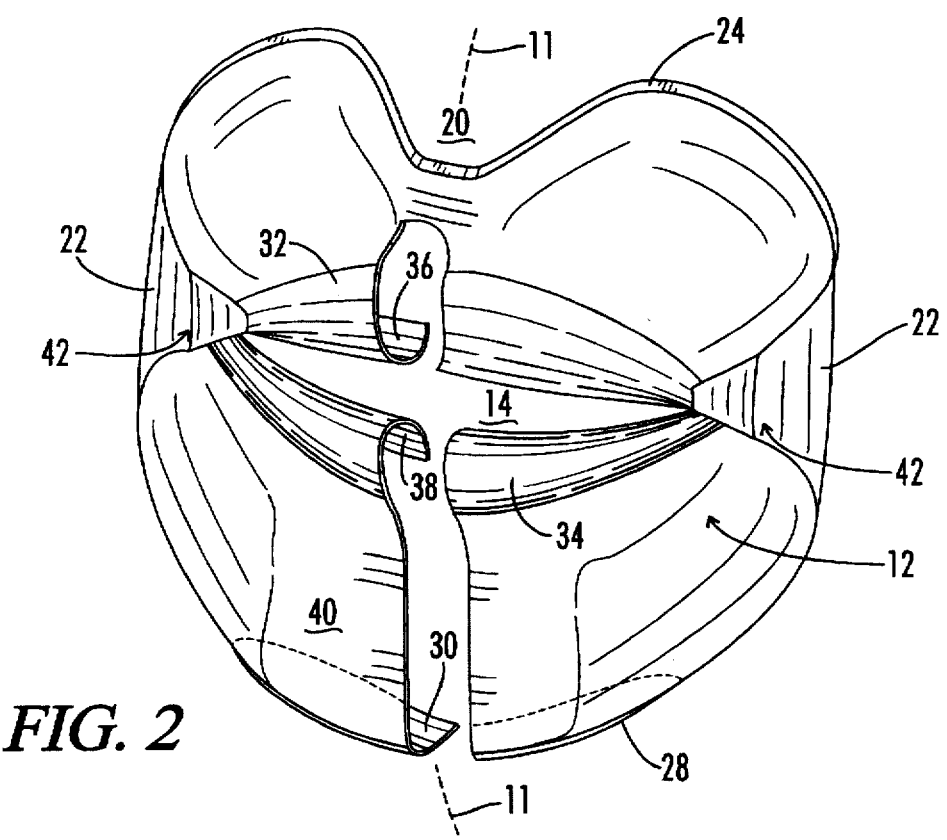
FIG. 2 is a perspective view of the lip and chin protector of the present invention wherein a section is taken along the mid-line to depict the upper and lower securing flanges of the protector of the present invention.

Referring particularly to FIGS. 1 and 2, barrier section 12 comprises chin covering section 16, upper flange 18, and upper and lower lip shields 32 and 34. Upper flange 18 includes upper edge 24. Positioned along the mid-line 11 of protector 10 and formed within upper edge 24 of upper flange 18 is nose groove 20. Nose groove 20 enables the user to wear protector 10 without impairing breathing as the user's nose fits within nose groove 20 when protector 10 is worn.

Chin covering section 16 includes a lower edge 28. As best seen in FIG. 2, chin covering section 16 includes chin flange 30 which projects from the front surface 40 of chin covering section 16 toward the user and fits under the chin of the user. Chin flange 30 therefore extends from lower edge 28 of chin covering section 16.

Continuing on FIG. 2, positioned between chin covering section 16 and upper flange 18 are lip shield means comprising an upper lip shield 32 and lower lip shield 34. Formed through barrier 12 and between upper lip shield 32 and lower lip shield 34 is opening 14. Opening 14 is located so that it will be adjacent to the user's mouth when protector 10 is put on by the user. Flange means extend from the upper and lower lip shields 32 and 34 to secure the protector 10 in position on the user's face. Upper lip shield 32 proceeds toward opening 14 and continues through opening 14 to define upper securing flange 36. Thus, upper securing flange 36 protrudes to the rear of protector 10. Likewise, lower lip shield 34 proceeds through opening 14 to define lower securing flange 38. Thus, lower securing flange 38 protrudes to the rear of protector 10.

Continuing on FIGS. 1 and 2, upper edge 24 and lower edge 28 proceed away from the mid-line 11 of protector 10 to both the right and left sides of protector 10 to form medial lateral edges 26. Medial lateral edges 16 proceed toward and then away from the mid-line 11 of protector 10 to create indentions 42 that lie adjacent to opening 14.

Mounted within indentions 42 and between upper flange 18 and chin covering section 16 is flexible area 22. Flexible area 22 enables the user to open and close opening 14 when protector 10 is worn.

Figure 3:
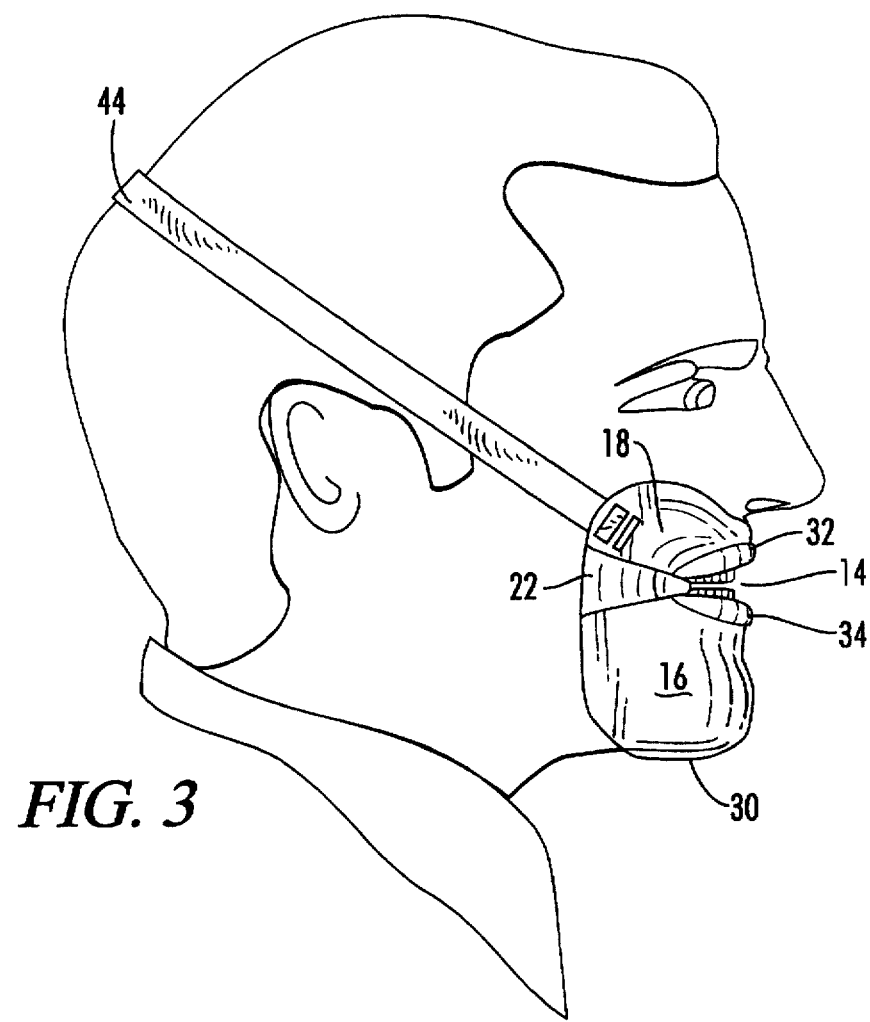
FIG. 3 is a side view of the present invention when mounted to a patient.
Figure 4:
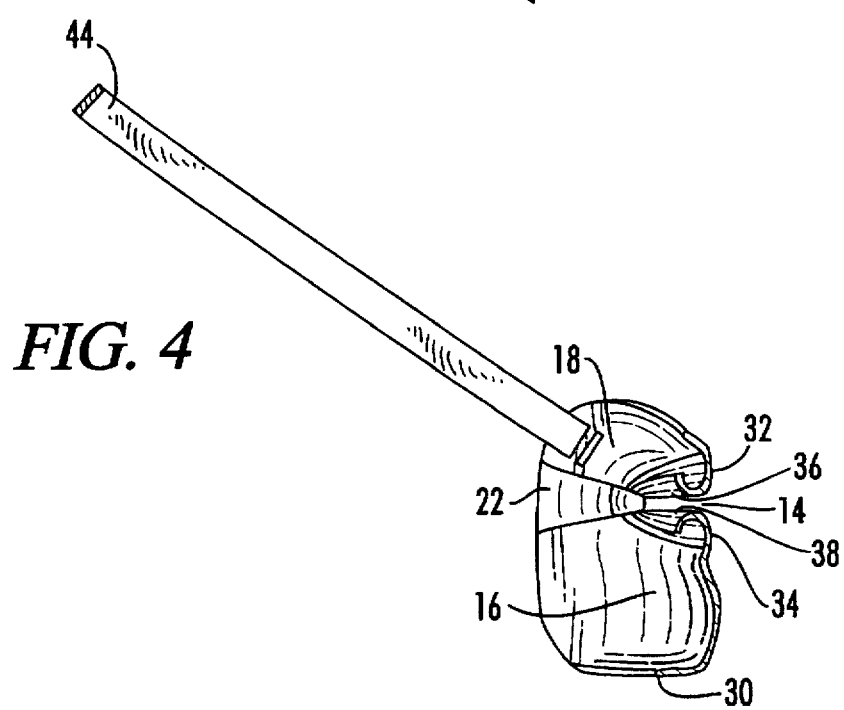
FIG. 4 is a side sectional view of the protector of the present invention.

Referring now to FIGS. 3 and 4, the application of protector 10 by the user can be more fully described. The user wears protector 10 so that upper flange 18 fits between the user's lip and the user's nose and chin covering section 16 fits over the user's chin. Upper and lower securing flanges 36 and 38 are fired behind user's upper and lower lips so that upper lip shield 32 and lower lip shield 34 can protect the user's lips. Additionally, upper and lower securing flanges 36 and 38 secure protector 10 in its desired position. Chin flange 30 also secures protector 10 in its desired position. Finally, as best seen in FIG. 3, flexible area 22 is adjacent to the user's mouth so that the user can open and close his mouth when wearing protector 10. This feature enables the user to eat, drink and talk through opening 14 while wearing protector 10. Thus, in the preferred embodiment of this invention, upper and lower securing flanges 36 and 38 and chin flange 30 secure protector 10 in its desired position.

Additionally, as shown in FIGS. 3 and 4, the protector 10 of this invention can include a strap 44 to further secure protector 10 in its desired position.

Protector 10 can be comprised entirely of a flexible rubber material, such as latex. Thus, flexible area 22 will also be comprised of latex. Alternatively, all areas of protector 10 except flexible area 22 can comprise a rigid plastic material, such as a polycarbonate. In this case, flexible area 22 continues to comprise a flexible material such as a flexible rubber like latex. This embodiment of the invention can be formed by any suitable means or any means that would be apparent to one having ordinary skill in the art, including injection molding of the polycarbonate areas followed by adhesively mounting the flexible area 22 in its appropriate position. Further, when a rigid plastic material is used in the protector 10 of this invention, it is sufficiently thin so as to enable the user to open and close his mouth.

Thus, although there have been described particular embodiments of the present invention of a new and useful "Post-Surgery Lip and Chin Protector", it is not intended that such references be construed as limitations upon the scope of this invention except as set forth in the following claims. Further, although there have been described certain dimensions used in the preferred embodiment, it is not intended that such dimensions be construed as limitations upon the scope of this invention except as set forth in the following claims.

What I claim is:

1. A post-surgery lip and chin protector comprising:
   a. a barrier section for covering the lips and chin of the user;
   b. an opening formed in the barrier section and defined by lip shield means for enabling unrestricted access to the user's mouth, wherein the opening is positioned to align with the user's mouth when the protector is worn;
   c. a flexible area positioned adjacent lateral medial edges of the barrier for facilitating unrestricted movement of the lips and jaw of the user; and
   d. means for securing the protector to the lips and chin of the user.

2. The protector according to claim 1 wherein the means for securing the barrier section to the lips and chin of the user comprises flange means extending rearward from the barrier section into the opening and configured to cooperatively engage the user's lips.

3. The protector according to claim 1 further comprising a strap mounted to the barrier section, said strap adapted to fit around the users head.

4. The protector according to claim 1 wherein the means for securing the barrier section to the lips and the chin of the user further comprises a flange extending rearward from a lower edge of the barrier section, wherein the flange is contoured to the user's chin.

5. A post-surgery lip and chin protector comprising:
   a. a barrier section configured to directly engage and cover the lips, chin and facial area immediately adjacent thereto;
   b. an opening formed in the barrier section and defined by an upper lip shield and a lower lip shield, wherein the upper and lower lip shields project into the opening and enable unrestricted access to the user's mouth;
   c. first and second flexible areas positioned immediately adjacent the upper and lower lip shields for facilitating unrestricted movement of the lips and jaw of the user; and
   d. flange means extending from the upper and lower lip shields for retaining the protector in position.

6. The lip and chin protector of claim 5, further comprising:
   flange means extending from a lower edge of the barrier section and configured to engage the chin of the user.

7. The lip and chin protector of claim 5, further comprising:
   a strap attached to the barrier section.

8. The lip and chin protector of claim 5, further comprising:
   a notch formed along an upper edge of the barrier section and configured to receive the lower portion of the user's nose.

9. A post-surgery lip and chin protector, comprising:
   a. a barrier configured to cover the lips and chin of a user;
   b. an opening formed in the barrier and positioned to align with the user's mouth, wherein the opening enables unrestricted access to the mouth of the user;
   c. lip shield means positioned immediately adjacent the opening and configured to engage the user's lips;
   d. first and second indentions formed along medial lateral edges of the barrier; and
   e. first and second flexible areas positioned within the first and second indentions and between an upper edge and a lower edge of the barrier for facilitating unrestricted movement of the lips and jaw.

10. The protector of claim 9, further comprising:
    flange means projecting from a lower edge of the protector and configured to follow the contour of the user's chin for retaining the protector in position.

11. The protector of claim 9, further comprising:
    flange means projecting from the lip shield means for securing the protector about the lips of the user.

12. The protector of claim 9, further comprising:
    a strap attached to the barrier and configured to encircle the head of the user for retaining the protector in position.

* * * * *